United States Patent
Magni et al.

(10) Patent No.: US 10,534,005 B2
(45) Date of Patent: Jan. 14, 2020

(54) METHOD FOR THE IN VITRO DIAGNOSIS OF THYROID DISEASES

(71) Applicant: UNIVERSITA' DEGLI STUDI DI MILANO—BICOCCA, Milan (IT)

(72) Inventors: Fulvio Magni, Milan (IT); Fabio Pagni, Milan (IT); Clizia Chinello, Milan (IT); Gabriele De Sio, Milan (IT)

(73) Assignee: UNIVERSITA'DELGI STUDI DI MILANO-BICOCCA (IT)

( * ) Notice: Subject to any disclaimer, the term of this patent is extended or adjusted under 35 U.S.C. 154(b) by 0 days.

(21) Appl. No.: 15/768,626

(22) PCT Filed: Oct. 14, 2016

(86) PCT No.: PCT/IB2016/056171
§ 371 (c)(1),
(2) Date: Apr. 16, 2018

(87) PCT Pub. No.: WO2017/064664
PCT Pub. Date: Apr. 20, 2017

(65) Prior Publication Data
US 2018/0306816 A1   Oct. 25, 2018

(30) Foreign Application Priority Data

Oct. 16, 2015 (IT) .................. 102015000062301

(51) Int. Cl.
| | | |
|---|---|---|
| G01N 33/78 | (2006.01) | |
| F25B 25/00 | (2006.01) | |
| G01N 33/68 | (2006.01) | |
| G01N 33/574 | (2006.01) | |

(52) U.S. Cl.
CPC .......... *G01N 33/78* (2013.01); *F25B 25/005* (2013.01); *G01N 33/68* (2013.01); *G01N 33/6851* (2013.01); *G01N 33/6893* (2013.01); *F25B 2339/047* (2013.01); *G01N 33/57407* (2013.01); *G01N 2800/046* (2013.01)

(58) Field of Classification Search
CPC ....... G01N 2800/046; G01N 33/57407; G01N 33/68; G01N 33/6851; G01N 33/6893; G01N 33/78
See application file for complete search history.

(56) References Cited

U.S. PATENT DOCUMENTS

| | | |
|---|---|---|
| 2007/0087448 A1 | 4/2007 | Nelsestuen |
| 2011/0275065 A1 | 11/2011 | Walfish et al. |

FOREIGN PATENT DOCUMENTS

| | | |
|---|---|---|
| WO | 2005/079410 | 9/2005 |
| WO | 2009/111881 | 9/2009 |
| WO | 2014/189467 | 11/2014 |

OTHER PUBLICATIONS

International Search Report and Written Opinion corresponding to International Patent Application No. PCT/IB2016/056171, dated Apr. 25, 2017.
Pagni et al., "Proteomics for the diagnosis of thyroid lesions: preliminary report.", Cytopathology, vol. 26, No. 5, Jul. 20, 2014, pp. 318-324, XP055275833.
Park et al., "Diagnostic Value of Galectin-3, HBME-1, Cytokeratin 19, High Molecular Weight Cytokeratin, Cyclin D1 and p27kip1 in the Differential Diagnosis of Thyroid Nodules", J. Korean Med Sci, Jan. 1, 2007, pp. 621-628, XP055342058.
Kyueng-Whan Min et al., "Imaging Mass Spectrometry in Papillary Thyroid Carcinoma for the Identification and Validation of Biomarker Proteins", Journal of Korean Medical Science, vol. 29, No. 7, Jan. 1, 2014, p. 934, XP055341730.
Janete M. Cerutti et al., "A preoperative diagnostic test that distinguishes benign from malignant thyroid carcinoma based on gene expression", Journal of Clinical Investigation, vol. 113, No. 8, Apr. 15, 2004, pp. 1234-1242, XP055042033.
Leandro Luongo de Matos et al., "Expression of ck-19, galectin-3 and hbme-1 in the differentiation of thyroid lesions: systematic review and diagnostic meta-analysis", Diagnostic Pathology, vol. 7, No. 1, Aug. 13, 2012, p. 97, XP021129551.
Catherine B. Barden et al, "Classification of Follicular Thyroid Tumors by Molecular Signature: Results of Gene Profiling 1 Departments of Surgery", Clinical Cancer Research, May 1, 2003, XP055341955.
Pagni Fabio et al., "Proteomics in thyroid cytopathology: Relevance of MALDI-imaging in distinguishing malignant from benign lesions." Proteomics, vol. 16, No. 11-12, Jun. 2016, pp. 1775-1784, XP002766750.

*Primary Examiner* — Marcela M Cordero Garcia

(74) *Attorney, Agent, or Firm* — McAndrews, Held & Malloy, Ltd.

(57) ABSTRACT

A method for the in vitro differential diagnosis of thyroid diseases is described comprising the step of determining by means of mass spectrometry in a biological sample the variation in intensity of at least one of the peaks (m/z)±0.3% selected from the group consisting of 10129 Th, 9749 Th, 10092 Th, 7935 Th, 4620 Th, 4748 Th, 8565 Th, 7565 Th, 4518 Th, 7936 Th, 5044 Th, 6699 Th, 11310 Th, 12277 Th, 6805 Th, 6880 Th, 8566 Th, 8309 Th, 5564 Th, 9711 Th, 7263 Th, 10296 Th and 4353 Th and/or of at least one of the peaks (m/z)±0.3% selected from the group consisting of 4987 Th, 7110 Th, 4804 Th, 9957 Th, 6719 Th, 4372 Th, 4196 Th, 4111 Th, 4282 Th, 5935 Th and 5519 Th.

3 Claims, No Drawings

Specification includes a Sequence Listing.

ical Patent Application No. PCT/IB2016/056171, which was filed Oct. 14, 2016, claiming the benefit of priority to Italian Patent Application No. 102015000062301, which was filed on Oct. 16, 2015. The entire text of the aforementioned applications is incorporated herein by reference in its entirety.

The present invention concerns a method for the in vitro differential diagnosis of thyroid diseases.

STATE OF THE ART

Cancer of the thyroid represents the most frequent malignant endocrine neoplasia and, due to the improvement in diagnostic capabilities and easier access to treatment, its incidence has grown significantly over the last decades. The well-differentiated carcinomas, like the papillary thyroid carcinoma (PTC) and the follicular thyroid carcinoma (FTC), represent 90% of all the malignant tumours of the thyroid and originate from the follicular epithelium, while the parafollicular C cells represent the precursor cells of a rare malignant entity: the medullar thyroid carcinoma (MTC). Other lesions which can currently be diagnosed by differential diagnostics are follicular thyroid adenoma (FTA) and Hashimoto's thyroiditis (HT), which instead represent benign entities that can present in the form of nodules.

Surgery is the treatment of choice for many tumours of the thyroid. The preoperative distinction between the benign and malignant conditions is therefore fundamental for avoiding unnecessary treatment of patients and morbidity connected with inappropriate surgery.

The instrument most widely used for preoperative diagnosis of nodules of the thyroid is fine needle aspiration (FNA). Unfortunately, a significant number of thyroid fine needle aspirations (20-30%) are "indeterminate for malignancy" (Thy3/Tir3 according to the international reporting classification) after the traditional pathological examination under optical microscope. This represents an important problem for these patients whose thyroid is surgically removed for diagnostic and non-curative purposes.

Therefore, in recent years, possible new diagnostic targets have been sought as a replacement for or in combination with those already in use.

In particular, genetic approaches have been developed, for example:

the analysis of fine needle aspirations for mutations of the genes BRAF, RAS, PAX8, RET etc.;

the analysis of fine needle aspirations by means of NGS (next generation sequencing) of a panel of 142 genes (Veracyte);

analysis of the expression of RNA on fine needle aspirations.

All these tests have a high cost and are not available in all countries.

A possible alternative is the use of a proteomic approach.

Pagni et al., Cytopathology (2014) describes a preliminary feasibility study on which an imaging technique is used, by means of mass spectrometry (matrix-assisted laser desorption/ionization (MALDI) imaging mass spectrometry (IMS)) to identify new proteomic targets of thyroid lesions, such as follicular lesions or medullary carcinoma. The above-mentioned article identifies some peaks (at 4965, 6278 and 6651 Th), the increase in intensity, of which, appears to be correlated with hyperplastic lesions. A further three peaks are also identified (at 7263, 8294 and 8310 Th), the increase in intensity, of which, appears to be correlated with Hürthle cell follicular adenoma.

Successive experimental tests by the same group, including the results illustrated in this description, subsequently showed that the above-mentioned peaks could be less significant when a higher number of samples are analysed. The need is therefore felt to identify proteomic profiles which are specific for the various forms of tumour of the thyroid and provide adequate reliability.

In particular, the need is felt to identify new markers of thyroid diseases to be used for diagnostic purposes for definition of the indeterminate forms today classified as Thy3.

Said objective aims to reduce the costs of the diagnostic thyroidectomies currently performed for the sole purpose of removing harmless nodules, which could be sent to clinical follow-up.

The object of the present invention is therefore to provide a method for in vitro differential diagnosis of thyroid diseases based on one or more peaks (m/z) and/or one or more specific reliable peptide biomarkers characteristic of each disease, which allows early, effective, quick and inexpensive diagnosis.

According to the present invention, said object is achieved by means of the method according to claim 1.

DETAILED DISCLOSURE OF THE INVENTION

The method for in vitro differential diagnosis of thyroid diseases according to the present invention comprises the step of determining in a biological sample by means of mass spectrometry the variation in intensity of at least one peak (m/z)±0.3% selected from the group consisting of 10129 Th, 9749 Th, 10092 Th, 7935 Th, 4620 Th, 4748 Th, 8565 Th, 7565 Th, 4518 Th, 7936 Th, 5044 Th, 6699 Th, 11310 Th, 12277 Th, 6805 Th, 6880 Th, 8566 Th, 8309 Th, 5564 Th, 9711 Th, 7263 Th, 10296 Th and 4353 Th and/or of at least one peak (m/z)±0.3% selected from the group consisting of 4987 Th, 7110 Th, 4804 Th, 9957 Th, 6719 Th, 4372 Th, 4196 Th, 4111 Th, 4282 Th, 5935 Th and 5519 Th.

The mean uncertainty on determination of the value m/z in the mass range considered is ±0.3%.

As can be deduced, the greater the number of peaks for which the intensity variation is determined, the lower the possibility of error in the diagnosis.

The peaks 4987 Th, 7110 Th, 4804 Th, 9957 Th, 6719 Th, 4372 Th, 4196 Th, 4111 Th, 4282 Th, 5935 Th and 5519 Th correspond respectively to the following peptides: cathepsin B (SEQ ID NO:1), histone H2B type 1-B/1-N (SEQ ID NO:2), coronin-1a (SEQ ID NO:3), phosphatidylethanolamine-binding protein 1 (SEQ ID NO:4) or glyceraldehyde-3-phosphate dehydrogenase (SEQ ID NO:5), histone H2A type 1-D/1-H/2-C (SEQ ID NO:6), 10 kDa mitochondrial heat shock protein (SEQ ID NO:7) or glyceraldehyde-3-phosphate dehydrogenase (SEQ ID NO:8), macrophage migration inhibitory factor (SEQ ID NO:9) or matrin-3 (SEQ ID NO:10) or heterogeneous nuclear ribonucleoproteins A2/B1 (SEQ ID NO:11) or cytoplasmic actin 2 (SEQ ID NO:12), galectin-3 OS=Homo sapiens GN=LGALS3 PE=1 SV=5 (SEQ ID NO:13) or histone H2B type 3-B/1-J/1-B (SEQ ID NO:14), heterogeneous nuclear ribonucleoproteins A2/B1 (SEQ ID NO:15) or hepatoma-derived growth factor (SEQ ID NO:16), fructose-biphosphate aldolase A (SEQ ID NO:17) and mitochondrial Lon protease homolog (SEQ ID NO:18).

In one embodiment, the method for in vitro differential diagnosis of thyroid diseases according to the present invention comprises the steps of: measuring the levels of at least one biomarker selected from the group consisting of cathepsin B (SEQ ID NO:1), histone H2B type 1-B/1-N (SEQ ID NO:2), coronin-1a (SEQ ID NO:3), phosphatidylethanolamine-binding binding protein 1 (SEQ ID NO:4), glyceraldehyde-3-phosphate dehydrogenase (SEQ ID NO:5), histone H2A type 1-D/1-H/2-C (SEQ ID NO:6), 10 kDa mitochondrial heat shock protein (SEQ ID NO:7), glyceraldehyde-3-phosphate dehydrogenase (SEQ ID NO:8), macrophage migration inhibitory factor (SEQ ID NO:9), matrin-3 (SEQ ID NO:10), heterogeneous nuclear ribonucleoproteins A2/B1 (SEQ ID NO:11), cytoplasmic actin 2 (SEQ ID NO:12), galectin-3 OS=Homo sapiens GN=LGALS3 PE=1 SV=5 (SEQ ID NO:13), histone H2B type 3-B/1-J/1-B (SEQ ID NO:14), heterogeneous nuclear ribonucleoproteins A2/B1 (SEQ ID NO:15), hepatoma-derived growth factor (SEQ ID NO:16), fructose-biphosphate aldolase A (SEQ ID NO:17) and mitochondrial Lon protease homolog (SEQ ID NO:18), and correlating the measurement with a specific thyroid disease.

One preferred embodiment determines the variation in intensity of all the peaks (m/z) 10129 Th, 9749 Th, 10092 Th, 7935 Th, 4620 Th, 4748 Th, 8565 Th, 7565 Th, 4518 Th, 7936 Th, 5044 Th, 6699 Th, 11310 Th, 12277 Th, 6805 Th, 6880 Th, 8566 Th, 8309 Th, 5564 Th, 9711 Th, 7263 Th, 10296 Th and 4353 Th or of all the peaks (m/z) 4987 Th, 7110 Th, 4804 Th, 9957 Th, 6719 Th, 4372 Th, 4196 Th, 4111 Th, 4282 Th, 5935 Th and 5519 Th.

In an even more preferred embodiment determines the variation in intensity of all the peaks (m/z) 10129 Th, 9749 Th, 10092 Th, 7935 Th, 4620 Th, 4748 Th, 8565 Th, 7565 Th, 4518 Th, 7936 Th, 5044 Th, 6699 Th, 11310 Th, 12277 Th, 6805 Th, 6880 Th, 8566 Th, 8309 Th, 5564 Th, 9711 Th, 7263 Th, 10296 Th e 4353 Th, 4987 Th, 7110 Th, 4804 Th, 9957 Th, 6719 Th, 4372 Th, 4196 Th, 4111 Th, 4282 Th, 5935 Th and 5519 Th.

The mass spectrometry used to determine the variation in intensity of one or more of the above-mentioned peaks (m/z) in the biological sample is preferably MALDI-MSI (Matrix Assisted Laser Desorption Mass Spectrometry Imaging).

The biological sample is preferably a thyroid cytological smear.

The differential diagnosis made possible by the method according to the invention is preferably between a benign thyroid disease and a malignant thyroid disease, more preferably between papillary thyroid carcinoma, Hashimoto's thyroiditis, hyperplastic lesion and follicular adenoma, in a biological sample not classifiable for certain as malignant or benign by means of cytological analysis under a microscope.

EXAMPLES (Table 2)

13 ex vivo cytological smears of cells with a certainly benign morphological appearance (benign morphological class Thy2 comprising 9 hyperplastic lesions—Hp, and 4 Hashimoto's thyroiditis—HT), 13 smears of cells with a strongly suspect/certainly malignant appearance (malignant cytological class Thy4 obtained from Papillary Thyroid Carcinomas—PTC-) and 10 uncertain so-called indeterminate smears (8 probably benign and 2 probably malignant) were used.

The thyroid cytological samples were deposited on a slide covered with indium tin oxide (ITO). Each slide was thawed in a vacuum for 30 minutes, then washed with increasing concentrations of ethanol (70 to 100%) and then covered with matrix (sinapinic acid) by means of ImagePrep (Bruker Daltonics, Brema, Germany). All the mass spectra were acquired in linear positive mode in the mass range of 3,000-25,000 Th, with a mass spectrometer UltrafleXtreme (Bruker Daltonics, Brema Germany), provided with a Smartbeam (Nd: YAG/355 nm) laser, operating at a frequency of 2 kHz. The spectra were collected with a laser diameter of approximately 50 μm and with a spatial resolution of 80 μm. After the MALDI analysis, the matrix was removed with increasing concentrations of EtOH (70% and 100%) and the slides were coloured with hematoxylin and eosin (H & E) or Giemsa. Lastly, the samples were converted into digital format by scanning with ScanScope CS digital scanner (Aperio, Parco Center Dr. Vista, Calif., USA), thus allowing direct overlapping of the cytological and proteomic images and therefore the integration of morphological characteristics with the molecular information obtained by means of MALDI-MSI on specific regions of interest (ROI).

The ROI were selected by a pathologist, giving priority to the areas with high density of homogeneous cells and excluding the areas with artifacts. The final histological diagnosis of the samples classified as indeterminate was not known by the personnel of the proteomic units and therefore the proteomic analyses were conducted completely blind. The proteic profiles obtained from these areas were statistically processed in order to characterise the specific thyroid lesions. The spectra of each ROI were selected by means of FlexImaging 3.0 (Bruker Daltonics, Brema, Germany), and imported in SCiLS Lab software 2014 (http://scils.de/, Brema, Germany) for their initial pre-processing steps: subtraction of the base line, smoothing, alignment and if necessary recalibration and normalization. The data were statistically processed for the construction of a diagnostic model evaluating various algorithms (SVM, Random Forrest, K nearest neighbours, Native Bayes, Classification tree, etc.).

Different models were constructed according to different algorithms. The result of the best model is given below, which allowed specific profiles to be obtained for the various forms of tumour of the thyroid.

The signals present in the proteic profiles of peptides identified (Table 1A) and those reported in table 1B were used to construct a diagnostic model which allows a correct classification to be made possibly also in cases of thyroid lesions with uncertain/doubtful diagnosis (so-called indeterminates or Thy3, Table 2).

The characteristics of the diagnostic model constructed using the signals of Tables 1A and 1B are:
Sensitivity: 0.94
Specificity: 1.00
AUC: 0.98

TABLE 1A list of the signals (m/z MSI) identified (ID protein) used to construct the diagnostic model. The right-hand column shows the exact value of the peptide identified (m/z ID).

| m/z MSI (±0.3%) | ID protein | SEQ ID NO: | m/z ID* |
|---|---|---|---|
| 4987 | Cathepsin B | 1 | 4978.4 |
| 7110 | Histone H2B type 1-B/1-N | 2 | 7091.0 |
| 4804 | Coronin-1A | 3 | 4805.3 |
| 9957 | Phosphatidylethanolamine-binding protein 1 | 4 | 9967.1 |
| | Glyceraldehyde-3-phosphate dehydrogenase | 5 | 9945.0 |

TABLE 1A-continued list of the signals (m/z MSI) identified (ID protein) used to construct the diagnostic model. The right-hand column shows the exact value of the peptide identified (m/z ID).

| m/z MSI (±0.3%) | ID protein | SEQ ID NO: | m/z ID* |
|---|---|---|---|
| 6719 | Histone H2A type 1-D/1-H/2-C | 6 | 6713.8 |
| 4372 | 10 kDa mitochondrial heat shock protein | 7 | 4376.29 |
| | Glyceraldehyde-3-phosphate dehydrogenase | 8 | 4376.12 |
| | Macrophage migration inhibitory factor | 9 | 4198.2 |
| 4196 | Matrin-3 | 10 | 4187.1 |
| | Heterogeneous nuclear ribonucleoproteins A2/B1 | 11 | 4202.6 4186.1 |
| | Cytoplasmic actin 2 | 12 | |
| 4111 | Galectin-3 OS = *Homo sapiens* GN = LGALS3 PE = 1 SV = 5 | 13 | 4105.2 |
| | Histone H2B type 3-B/1-J/1-B | 14 | 4100.1 |
| 4282 | Heterogeneous nuclear ribonucleoproteins A2/B1 | 15 | 4289.5 |
| | Hepatoma-derived growth factor | 16 | 4293.8 |
| 5935 | Fructose-biphosphate aldolase A | 17 | 5927.0 |
| 5519 | Mitochondrial Lon protease homolog | 18 | 5520.6 |

*m/z ID = exact value of peptide identified

TABLE 1B

List of signals (m/z) used to construct the diagnostic model
Peaks (m/z)

10129
9749
10092
7935
4620
4748
8565
7565
4518
7936
5044
6699
11310
12277
6805
6880
8566
8309
5564
9711
7263
10296
4353

TABLE 2

| Traditional microscope diagnosis of smear | MALDI classification |
|---|---|
| Benign Hp (TIR2) | Benign |
| Benign Hp (TIR2) | Benign |
| Benign Hp (TIR2) | Benign |
| Benign Hp (TIR2) | Benign |
| Benign Hp (TIR2) | Benign |
| Benign Hp (TIR2) | Benign |
| Benign Hp (TIR2) | Benign |
| Benign Hp (TIR2) | Benign |
| Benign Hp (TIR2) | Benign |
| Benign HT (TIR2) | Benign |
| Benign HT (TIR2) | Benign |
| Benign HT (TIR2) | Benign |
| Benign HT (TIR2) | Benign |
| Uncertain/benign HT (TIR3) | Benign |
| Uncertain/benign HT (TIR3) | Malignant |
| Uncertain/benign Hp (TIR3) | Benign |
| Uncertain/benign Hp (TIR3) | Benign |
| Uncertain/benign FA (TIR3) | Benign |
| Uncertain/benign FA (TIR3) | Benign |
| Uncertain/benign FA (TIR3)) | Benign |
| Uncertain/benign FA (TIR3)) | Benign |
| Uncertain/malignant fv PTC (TIR3) | Malignant |
| Uncertain/malignant fv PTC (TIR3) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |
| Suspect malignancy (TIR4) | Malignant |

It should be noted that the peaks of Table 1B were more informative than those of Table 1A. The combination of the peaks of Tables 1A and 1B was even more informative than the peaks of the two single groups taken individually.

From the data reported above, the advantages of the method according to the invention are evident.

In particular, the method according to the present invention allows the recognition of at least two distinct proteomic profiles, benign and malignant, in samples with indeterminate classification Thy3, potentially reducing in the future, the cases of unnecessary removal of the thyroid.

Furthermore, the method according to the present invention also allows distinction between papillary thyroid carcinoma, Hashimoto's thyroiditis, hyperplastic lesion and follicular adenoma in a biological sample not classifiable for certain by means of traditional cytological analysis.

The invention claimed is:

1. A method for the in vitro differential diagnosis of thyroid diseases selected from the group consisting of papillary thyroid carcinoma, Hashimoto's thyroiditis, hyperplastic lesion, and follicular adenoma comprising the step of using Matrix Assisted Laser Desorption Mass Spectrometry Imaging (MALDI-MSI) to assess a thyroid cytological smear to determine the variation in intensity of the group of peaks (m/z) consisting of 10129 Th, 9749 Th, 10092 Th, 7935 Th, 4620 Th, 4748 Th, 8565 Th, 7565 Th, 4518 Th, 7936 Th, 5044 Th, 6699 Th, 11310 Th, 12277 Th, 6805 Th, 6880 Th, 8566 Th, 8309 Th, 5564 Th, 9711 Th, 7263 Th, 10296 Th and 4353 Th and of the group of peaks (m/z) ±0.3% consisting of 4987 Th, 7110 Th, 4804 Th, 9957 Th, 6719 Th, 4372 Th, 4196 Th, 4111 Th, 4282 Th, 5935 Th and 5519 Th.

2. The method of claim 1, wherein the peaks (m/z) 4987 Th, 7110 Th, 4804 Th, 9957 Th, 6719 Th, 4372 Th, 4196 Th, 4111 Th, 4282 Th, 5935 Th and 5519 Th respectively correspond to the biomarkers cathepsin B (SEQ ID NO:1), histone H2B type 1-B/1-N (SEQ ID NO:2), coronin-1A (SEQ ID NO:3), phosphatidylethanolamine-binding protein 1 (SEQ ID NO:4) or glyceraldehyde-3-phosphate dehydrogenase (SEQ ID NO:5), histone H2A type 1-D/1-H/2-C (SEQ ID NO:6), 10 kDa mitochondrial heat shock protein (SEQ ID NO:7) or glyceraldehyde-3-phosphate dehydrogenase (SEQ ID NO:8), macrophage migration inhibitory factor (SEQ ID NO:9) or matrin-3 (SEQ ID NO:10) or heterogeneous nuclear ribonucleoproteins A2/B1 (SEQ ID NO:11) or cytoplasmic actin 2 (SEQ ID NO:12), galectin-3 OS=Homo sapiens GN=LGALS3 PE=1 SV=5 (SEQ ID NO:13) or histone H2B type 3-B/1-J/1-B (SEQ ID NO:14), heterogeneous nuclear ribonucleoproteins A2/B1 (SEQ ID NO:15) or hepatoma-derived growth factor (SEQ ID NO:16), fructose-bisphosphate aldolase A (SEQ ID NO:17) and mitochondrial Lon protease homolog (SEQ ID NO:18).

3. The method of claim 1, wherein the differential diagnosis is between a benign thyroid disease and a malignant thyroid disease in a thyroid cytological smear not classifiable for certain as malignant or benign by microscope cytological analysis.

* * * * *

SEQUENCE LISTING

<160> NUMBER OF SEQ ID NOS: 18

<210> SEQ ID NO 1
<211> LENGTH: 44
<212> TYPE: PRT
<213> ORGANISM: Homo sapiens

-continued

<400> SEQUENCE: 1

Gly Thr Pro Tyr Trp Leu Val Ala Asn Ser Trp Asn Thr Asp Trp Gly
1               5                   10                  15

Asp Asn Gly Phe Phe Lys Ile Leu Arg Gly Gln Asp His Cys Gly Ile
            20                  25                  30

Glu Ser Glu Val Val Ala Gly Ile Pro Arg Thr Asp
        35                  40

<210> SEQ ID NO 2
<211> LENGTH: 64
<212> TYPE: PRT
<213> ORGANISM: Homo sapiens

<400> SEQUENCE: 2

Met Asn Ser Phe Val Asn Asp Ile Phe Glu Arg Ile Ala Gly Glu Ala
1               5                   10                  15

Ser Arg Leu Ala His Tyr Asn Lys Arg Ser Thr Ile Thr Ser Arg Glu
            20                  25                  30

Ile Gln Thr Ala Val Arg Leu Leu Pro Gly Glu Leu Ala Lys His
            35                  40                  45

Ala Val Ser Glu Gly Thr Lys Ala Val Thr Lys Tyr Thr Ser Ser Lys
50                  55                  60

<210> SEQ ID NO 3
<211> LENGTH: 41
<212> TYPE: PRT
<213> ORGANISM: Homo sapiens

<400> SEQUENCE: 3

Arg Ser Ser Lys Phe Arg His Val Phe Gly Gln Pro Ala Lys Ala Asp
1               5                   10                  15

Gln Cys Tyr Glu Asp Val Arg Val Ser Gln Thr Thr Trp Asp Ser Gly
            20                  25                  30

Phe Cys Ala Val Asn Pro Lys Phe Val
            35                  40

<210> SEQ ID NO 4
<211> LENGTH: 89
<212> TYPE: PRT
<213> ORGANISM: Homo sapiens

<400> SEQUENCE: 4

Pro Val Asp Leu Ser Lys Trp Ser Gly Pro Leu Ser Leu Gln Glu Val
1               5                   10                  15

Asp Glu Gln Pro Gln His Pro Leu His Val Thr Tyr Ala Gly Ala Ala
            20                  25                  30

Val Asp Glu Leu Gly Lys Val Leu Thr Pro Thr Gln Val Lys Asn Arg
            35                  40                  45

Pro Thr Ser Ile Ser Trp Asp Gly Leu Asp Ser Gly Lys Leu Tyr Thr
50                  55                  60

Leu Val Leu Thr Asp Pro Asp Ala Pro Ser Arg Lys Asp Pro Lys Tyr
65                  70                  75                  80

Arg Glu Trp His His Phe Leu Val Val
                85

<210> SEQ ID NO 5
<211> LENGTH: 90
<212> TYPE: PRT
<213> ORGANISM: Homo sapiens

<400> SEQUENCE: 5

Ala Ile Asn Asp Pro Phe Ile Asp Leu Asn Tyr Met Val Tyr Met Phe
1               5                   10                  15

Gln Tyr Asp Ser Thr His Gly Lys Phe His Gly Thr Val Lys Ala Glu
            20                  25                  30

Asn Gly Lys Leu Val Ile Asn Gly Asn Pro Ile Thr Ile Phe Gln Glu
        35                  40                  45

Arg Asp Pro Ser Lys Ile Lys Trp Gly Asp Ala Gly Ala Glu Tyr Val
    50                  55                  60

Val Glu Ser Thr Gly Val Phe Thr Thr Met Glu Lys Ala Gly Ala His
65                  70                  75                  80

Leu Gln Gly Gly Ala Lys Arg Val Ile Ile
                85                  90

<210> SEQ ID NO 6
<211> LENGTH: 61
<212> TYPE: PRT
<213> ORGANISM: Homo sapiens

<400> SEQUENCE: 6

Val Leu Glu Tyr Leu Thr Ala Glu Ile Leu Glu Leu Ala Gly Asn Ala
1               5                   10                  15

Ala Arg Asp Asn Lys Lys Thr Arg Ile Ile Pro Arg His Leu Gln Leu
            20                  25                  30

Ala Ile Arg Asn Asp Glu Glu Leu Asn Lys Leu Leu Gly Lys Val Thr
        35                  40                  45

Ile Ala Gln Gly Gly Val Leu Pro Asn Ile Gln Ala Val
    50                  55                  60

<210> SEQ ID NO 7
<211> LENGTH: 39
<212> TYPE: PRT
<213> ORGANISM: Homo sapiens

<400> SEQUENCE: 7

Ser Val Lys Val Gly Asp Lys Val Leu Leu Pro Glu Tyr Gly Gly Thr
1               5                   10                  15

Lys Val Val Leu Asp Asp Lys Asp Tyr Phe Leu Phe Arg Asp Gly Asp
            20                  25                  30

Ile Leu Gly Lys Tyr Val Asp
        35

<210> SEQ ID NO 8
<211> LENGTH: 42
<212> TYPE: PRT
<213> ORGANISM: Homo sapiens

<400> SEQUENCE: 8

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe
        35                  40

<210> SEQ ID NO 9
<211> LENGTH: 39
<212> TYPE: PRT

<213> ORGANISM: Homo sapiens

<400> SEQUENCE: 9

Pro Met Phe Ile Val Asn Thr Asn Val Pro Arg Ala Ser Val Pro Asp
1               5                   10                  15

Gly Phe Leu Ser Glu Leu Thr Gln Gln Leu Ala Gln Ala Thr Gly Lys
            20                  25                  30

Pro Pro Gln Tyr Ile Ala Val
        35

<210> SEQ ID NO 10
<211> LENGTH: 38
<212> TYPE: PRT
<213> ORGANISM: Homo sapiens

<400> SEQUENCE: 10

Leu Asn Lys Ile Asn Glu Ala Phe Ile Glu Met Ala Thr Thr Glu Asp
1               5                   10                  15

Ala Gln Ala Ala Val Asp Tyr Tyr Thr Thr Thr Pro Ala Leu Val Phe
            20                  25                  30

Gly Lys Pro Val Arg Val
        35

<210> SEQ ID NO 11
<211> LENGTH: 40
<212> TYPE: PRT
<213> ORGANISM: Homo sapiens

<400> SEQUENCE: 11

Asn Gln Gly Gly Gly Tyr Gly Gly Tyr Asp Asn Tyr Gly Gly Gly
1               5                   10                  15

Asn Tyr Gly Ser Gly Asn Tyr Asn Asp Phe Gly Asn Tyr Asn Gln Gln
            20                  25                  30

Pro Ser Asn Tyr Gly Pro Met Lys
        35                  40

<210> SEQ ID NO 12
<211> LENGTH: 36
<212> TYPE: PRT
<213> ORGANISM: Homo sapiens

<400> SEQUENCE: 12

Trp Ile Gly Gly Ser Ile Leu Ala Ser Leu Ser Thr Phe Gln Gln Met
1               5                   10                  15

Trp Ile Ser Lys Gln Glu Tyr Asp Glu Ser Gly Pro Ser Ile Val His
            20                  25                  30

Arg Lys Cys Phe
        35

<210> SEQ ID NO 13
<211> LENGTH: 42
<212> TYPE: PRT
<213> ORGANISM: Homo sapiens

<400> SEQUENCE: 13

Ser Ser Gly Gln Pro Ser Ala Thr Gly Ala Tyr Pro Ala Thr Gly Pro
1               5                   10                  15

Tyr Gly Ala Pro Ala Gly Pro Leu Ile Val Pro Tyr Asn Leu Pro Leu
            20                  25                  30

Pro Gly Gly Val Val Pro Arg Met Leu Ile 35                  40

<210> SEQ ID NO 14
<211> LENGTH: 36
<212> TYPE: PRT
<213> ORGANISM: Homo sapiens

<400> SEQUENCE: 14

Ser Ile Tyr Val Tyr Lys Val Leu Lys Gln Val His Pro Asp Thr Gly
1               5                   10                  15

Ile Ser Ser Lys Ala Met Gly Ile Met Asn Ser Phe Val Asn Asp Ile
                20                  25                  30

Phe Glu Arg Ile
                35

<210> SEQ ID NO 15
<211> LENGTH: 41
<212> TYPE: PRT
<213> ORGANISM: Homo sapiens

<400> SEQUENCE: 15

Asn Gln Gly Gly Gly Tyr Gly Gly Tyr Asp Asn Tyr Gly Gly
1               5                   10                  15

Asn Tyr Gly Ser Gly Asn Tyr Asn Asp Phe Gly Asn Tyr Asn Gln Gln
                20                  25                  30

Pro Ser Asn Tyr Gly Pro Met Lys Ser
                35                  40

<210> SEQ ID NO 16
<211> LENGTH: 38
<212> TYPE: PRT
<213> ORGANISM: Homo sapiens

<400> SEQUENCE: 16

Ser Glu Pro Gly Ser Gly Arg Gly Pro Pro Gln Glu Glu Glu Glu Glu
1               5                   10                  15

Glu Asp Glu Glu Glu Glu Ala Thr Lys Glu Asp Ala Glu Ala Pro Gly
                20                  25                  30

Ile Arg Asp His Glu Ser
                35

<210> SEQ ID NO 17
<211> LENGTH: 56
<212> TYPE: PRT
<213> ORGANISM: Homo sapiens

<400> SEQUENCE: 17

Ser Ala Leu Lys Ala Trp Gly Gly Lys Lys Glu Asn Leu Lys Ala Ala
1               5                   10                  15

Gln Glu Glu Tyr Val Lys Arg Ala Leu Ala Asn Ser Leu Ala Cys Gln
                20                  25                  30

Gly Lys Tyr Thr Pro Ser Gly Gln Ala Gly Ala Ala Ser Glu Ser
                35                  40                  45

Leu Phe Val Ser Asn His Ala Tyr
        50                  55

<210> SEQ ID NO 18
<211> LENGTH: 60
<212> TYPE: PRT
<213> ORGANISM: Homo sapiens

<400> SEQUENCE: 18

```
Glu Ala Ser Ser Arg Gly Gly Ala Phe Ser Gly Gly Glu Asp Ala
1               5                   10                  15

Ser Glu Gly Gly Ala Glu Glu Gly Ala Gly Gly Ala Gly Gly Ser Ala
                20                  25                  30

Gly Ala Gly Glu Gly Pro Val Ile Thr Ala Leu Thr Pro Met Thr Ile
            35                  40                  45

Pro Asp Val Phe Pro His Leu Pro Leu Ile Ala Ile
        50                  55                  60
```